United States Patent
Tornes et al.

(10) Patent No.: US 9,579,405 B2
(45) Date of Patent: Feb. 28, 2017

(54) METHOD, COMPOUNDS AND PREPARATIONS FOR THE IDENTIFICATION OF SENTINEL LYMPH NODES

(71) Applicant: GE HEALTHCARE AS, Oslo (NO)

(72) Inventors: Audun Tornes, Oslo (NO); Jonnny Ostensen, Oslo (NO); Henrik Rasmussen, Heggedal (NO); Lars Hoff, Tolvsrod (NO)

(73) Assignee: GE Healthcare AS, Oslo (NO)

( * ) Notice: Subject to any disclaimer, the term of this patent is extended or adjusted under 35 U.S.C. 154(b) by 109 days.

(21) Appl. No.: 14/467,152

(22) Filed: Aug. 25, 2014

(65) Prior Publication Data

US 2014/0363381 A1 Dec. 11, 2014

Related U.S. Application Data

(63) Continuation of application No. 10/530,094, filed as application No. PCT/NO03/00328 on Oct. 1, 2003, now abandoned.

(30) Foreign Application Priority Data

Oct. 3, 2002 (NO) ................................ 20024755

(51) Int. Cl.
- *A61K 49/00* (2006.01)
- *A61K 49/22* (2006.01)
- *A61K 9/00* (2006.01)
- *A61K 9/50* (2006.01)

(52) U.S. Cl.
CPC .......... *A61K 49/223* (2013.01); *A61K 9/0009* (2013.01); *A61K 9/5015* (2013.01)

(58) Field of Classification Search
CPC .............................. A61K 49/00; A61K 49/223
See application file for complete search history.

(56) References Cited

U.S. PATENT DOCUMENTS

| | | | |
|---|---|---|---|
| 5,496,536 A | 3/1996 | Wolf | |
| 5,732,704 A | 3/1998 | Thurston et al. | |
| 6,221,337 B1 * | 4/2001 | Dugstad et al. | 424/9.52 |
| 6,444,192 B1 * | 9/2002 | Mattrey | 424/9.52 |
| 7,892,522 B2 | 2/2011 | Johnson et al. | 424/9.52 |
| 2001/0010811 A1 | 8/2001 | Rongved et al. | |
| 2002/0061280 A1 | 5/2002 | Mattrey | |
| 2002/0102217 A1 | 8/2002 | Hellebust et al. | |
| 2005/0142556 A1 | 6/2005 | Hoon et al. | 435/6 |

FOREIGN PATENT DOCUMENTS

| | | |
|---|---|---|
| WO | 00/38579 | 7/2000 |
| WO | 00/45855 | 8/2000 |
| WO | 01/12071 | 2/2001 |

OTHER PUBLICATIONS

Jurgen Maurer et al., Evaluaion of Metastases and Reactive Lymph Nodes in Doppler Sonography Using an Ultrasound Contrast Enhancer. Investigative Radiology. vol. 32(8), 441-446, 1997.*
Moriyasu, F. et.al. "Recent trends in ultrasound contrast agent", Innervision, Jan. 2002, vol. 17, No. 1, pp. 152-156.
Wisner, Erik R, et.al., "Contrast Enhanced Intermittent Power Doppler Ultrasound with Sub-micron Bubbles forsentinel Node Detection 1" Academic Radiology, vol. 9, No. 2, 2002 pp. S389-S391.
Mattrey, Robert F., et.al., "Sentinel Lymph Node Imaging with Microbubble Ultrasound Contrast Material 1" Academic Radiology, vol. 9, No. 1, 2002 pp. S231-S235.
Hoff, Lars, Acoustic Characterization of Contrast Agents for Medical Ultrasound Imaging, Kluwer Academic Publishers, 2001, Chapter 4, p. 99-109.
Oussoren, C., et.al. "Lymphatic Uptake and biodistribution of Liposomes after Subcutaneous Injection", Biochem. Biophys. Acta 1328 (1977), p. 261-272.
Shi, William T., et.al., "Destruction of Contrast Microbubbles and the Association with Inertial Cavitation", Ultrasound in Med. & Biol., vol. 26, 2000, p. 1-11.
International Search Report for PCT/2003/000328 dated Feb. 21, 2005.

* cited by examiner

Primary Examiner — Michael G Hartley
Assistant Examiner — Jagadishwar Samala
(74) Attorney, Agent, or Firm — Wood IP LLC

(57) ABSTRACT

The present invention relates to methods for the identification of a sentinel lymph node and to compounds and preparations used in said methods.

7 Claims, No Drawings

METHOD, COMPOUNDS AND PREPARATIONS FOR THE IDENTIFICATION OF SENTINEL LYMPH NODES

This application is a continuation filing of U.S. application Ser. No. 10/530,094 filed Jan. 26, 2006 which is a filing under 35 U.S.C. 371 of international application number PCT/NO2003/000328, filed Oct. 1, 2003, which claims priority to Norway application number 20024755 filed Oct. 3, 2002, the entire disclosure of which is hereby incorporated by reference.

This application is a continuation filing of U.S. application Ser. No. 10/530,094 filed Apr. 1, 2005 which is a filing under 35 U.S.C. 371 of international application number PCT/NO2003/000328, filed Oct. 1, 2003, which claims priority to Norway application number 20024755 filed Oct. 3, 2002, the entire disclosure of which is hereby incorporated by reference.

The present invention relates to methods for the identification of a sentinel lymph node and to compounds and preparations used in said methods.

The lymphatic system is made of vessels or ducts that begin in tissues and are designed to carry lymph fluid to local lymph nodes where the fluid is filtered and processed and sent to the next lymph node down the line until the fluid reaches the thoracic duct where it enters the blood stream. Lymph fluid which enters the lymph vessels carries with it substances and materials from the tissue, e.g. antigens, particles and cells. The lymph nodes process the lymph fluid by sieving it and macrophages inside the nodes remove particulate and cell material carried by the lymph fluid via phagocytosis.

When cancer occurs in tissues or organs, its loose matrix may allow the dislodging of cells that gain access to the lymphatic system, become trapped in the lymph node and grow. In early stages of cancer development in the node, the cancer remains limited to the node. However, in time, the nodal deposit can grow to totally replace the node and/or can spread downstream to the next node. The lymph nodes that drain the tissue or organ of interest (i.e., the cancerous tissue) are called the regional lymph nodes and the first node that traps the cancer is called the sentinel lymph node.

Patterns in the spread of tumours are complicated, as metastasis of neoplastic cells does not simply result in the spread of the neoplastic cells to the next physically nearest node. These nodes are more likely to contain the sentinel lymph node; however, the sentinel lymph node may be in a more distant nodal group. This can occur due to tumours, infections, injuries or previous treatment can block the lymph vessels that directly drain the tissue or organ of interest, promoting the development of aberrant pathways.

In the past, it has been normal practice in some situations to remove all lymph nodes potentially harbouring neoplastic cells metastasised from a tumour. A high morbidity rate is associated with this practice. Thus, several methods were developed to identify and biopsy the sentinel lymph node. If the sentinel lymph node is free of neoplastic cells, then further lymph node biopsies and (further) lymph node dissections can be avoided. Sentinel lymph nodes have been identified by injecting a marking agent into the tumour-bearing tissue and tracing the pathway of the marking system through the lymphatic system.

Visible marking agents such as dyes have been employed to visually detect the sentinel lymph node with the naked eye (A. E. Giuliano et al., Ann. Surg. 220, 1994, 391-401). Such a method requires significant surgical dissection. The nodes are indistinguishable from the surrounding tissue unless stained and the dyes unfortunately have an unpredictable and rapid clearance.

U.S. Pat. No. 5,732,704 discloses a method to detect sentinel lymph nodes using radiopharmaceutical compounds and the localisation of said compounds with the aid of a radiation detection probe. Although such compounds have a more delayed transit, patients and medical personnel are exposed to potentially harmful doses of ionising radiation. Radioactive isotopes also pose environmental contamination and disposal issues.

U.S. Pat. No. 5,496,536 describes a method of lymphography by using particles which are less than 1 μm in diameter and detecting those particles with different imaging modalities. As observed by C. Oussoren et al., Biochim Biophys. Acta 1328, 1997, 261-272, small particles are taken up into the lymphatic capillaries to a high extent; however, they are only poorly retained by lymph nodes. Such small particles are generally less effective ultrasound scatters and are hence not well suited for ultrasound based lymphography. Because of their poor retention by lymph nodes, they are not selective enough to detect only the sentinel lymph node, but will proceed on to other lymph nodes.

The observation made by Oussoren et al. was affirmed by the disclosures of WO-A-00/45855 and WO-A-00/38579.

WO-A-00/38579 discloses a method to detect sentinel lymph nodes using a contrast agent which is capable of migrating to the lymph node within a certain time frame—preferably within less than 3 hours—and detecting said contrast agent with an adequate detection modality. To migrate within this time frame, the contrast agent must comprise particles between 0.05 and 5 μm in diameter.

WO-A-00/45855 discloses a method to identify the sentinel lymph node using particulate contrast agents having a mean particle size of 1-10 μm and an imaging modality to detect said contrast agents in the lymph node.

As outlined in WO-A-00/38579 and WO-A-00/45855, the size of the contrast agent particles seems to have a significant impact on the operability of the methods disclosed in said documents. Unfortunately, the methods described do not work equally well with respect to the contrast agents and the imaging modalities employed. Although having about the same size, different contrast agents used for the same imaging modality behave significantly different, thus, the use of certain contrast agents in the methods described may result in insufficient sensitivity.

Accordingly, there is a need for a reliable method to identify the sentinel lymph node. Additionally, said method should be sensitive, safe and easy to carry out.

It has surprisingly been found that a method for the identification of a sentinel lymph node in a subject which comprises
a) administering to said subject a preparation comprising microbubbles comprising a shell and a gas or gas precursor, said microbubbles having a mean particle size of about 0.25-15 μm in diameter and a pressure stability of at least 50% at a pressure of 120 mm Hg,
b) allowing said microbubbles to accumulate in said sentinel lymph node and
c) detecting said microbubbles in said sentinel lymph node using ultrasound imaging
fulfils the criteria stated above.

Thus, the invention provides a method for the identification of a sentinel lymph node in a subject comprising
a) administering to said subject a preparation comprising microbubbles comprising a shell and a gas or gas precursor, said microbubbles having a mean particle size of about 0.25-15 µm in diameter and a pressure stability of at least 50% at a pressure of 120 mm Hg, b) allowing said microbubbles to accumulate in said sentinel lymph node and c) detecting said microbubbles in said sentinel lymph node using ultrasound imaging.

In another aspect, the invention is related to a method for the identification of a sentinel lymph node in a subject comprising detecting previously administered microbubbles in said sentinel lymph node of said subject using ultrasound imaging, wherein said microbubbles comprise a shell and a gas or gas precursor, have a mean particle size of about 0.25-15 µm in diameter and a pressure stability of at least 50% at a pressure of 120 mm Hg.

In yet another aspect, the invention is related to microbubbles for the identification of a sentinel lymph node which comprise a shell and a gas or gas precursor, have a mean particle size of about 0.25-15 µm in diameter and a pressure stability of at least 50% at a pressure of 120 mm Hg.

Another aspect of the invention are preparations for the identification of a sentinel lymph node comprising microbubbles comprising a shell and a gas or gas precursor, having a mean particle size of about 0.25-15 µm in diameter and a pressure stability of at least 50% at a pressure of 120 mm Hg.

Yet another aspect of the invention is the use of microbubbles comprising a shell and a gas or gas precursor, having a mean particle size of about 0.25-15 µm in diameter and a pressure stability of at least 50% at a pressure of 120 mm Hg for the manufacture of an agent for the identification of a sentinel lymph node.

The microbubbles according to the invention remain intact upon injection. They are not only easily taken up by the lymphatic system and the sentinel lymph node but they are also retained in the sentinel lymph node and remain stable, thus allowing sensitive and effective ultrasound detection.

In step a) of the method according to the invention, a preparation comprising microbubbles comprising a shell and a gas or gas precursor is administered to a subject. Said microbubbles have a mean particle size of about 0.25-15 µm in diameter and a pressure stability of at least 50% at a pressure of 120 mm Hg In the context of the present invention, "subject" means a vertebrate subject like a bird or a mammal and preferably a human.

The microbubbles and/or the preparations according to the invention should be biocompatible or not be physiologically deleterious or injurious to biological functions, and which will not result in any degree of unacceptable toxicity, including allergenic responses and disease states.

The microbubbles in the context of the invention comprise a shell and a gas or a gas precursor.

The term "shell" in the context of the present invention can be interchangeably used with the term "wall" or "membrane" and means material surrounding or defining a microbubble. The shell may be in the form of one or more layers, preferably in the form of a single monolayer or a bilayer (unilamellar), and the mono- or bilayer may be used to form one or more mono- or bilayers (oligo- or multilamellar). In the case of more than one mono- or bilayer, the mono- or bilayers are preferably concentric. Suitably, the shell is formulated from lipids, natural or synthetic polymeric materials, proteinaceous materials, carbohydrates, saccharides, and the like or combinations thereof. In a preferred embodiment, the shell has an overall negative or positive net charge. Thus, the shell may be composed of or comprise polymeric material or proteinaceous material having an excess of negative or positive charges or the shell may be composed of or comprise negatively or positively charged lipids. Alternatively, the shell may be composed of or comprise neutral polymeric, proteinaceous or lipid materials combined with incorporation or surface modification using negatively or positively charged components that give an overall net charge. Preferably, the shell is composed of or comprises lipids, more preferably phospholipids, e.g phosphatidylcholines, preferably dilauroyl phosphatidylcholine, dimyristoyl phosphatidylcholine, diheptadecanoyl phosphatidylcholine, dipalmitoyl phospatidylcholine, distearoyl phosphatidylcholine, diarachidoyl phosphatidylcholine or dibehenoyl phosphatidylcholine, phosphatidylserines, preferably dipalmitoyl or distearoyl phosphatidylserine, phosphatidylglycerols, preferably dipalmitoyl or distearoyl phosphatidylglycerol, phosphatidylethanolamines, preferably dipalmitoyl or distearoyl phosphatidylethanolamine, phosphatidylinositols, preferably dipalmitoyl or distearoyl phosphatidylinositol, phosphatidic acid, preferably dipalmitoyl or distearoyl phosphatidic acid, cardiolipins or any mixture of the foregoing named compounds, optionally in a mixture with cholesterol, cholesterol sulfate, cholesteryl hemisuccinate, N-palmitoyl homocystein, palmitic acid, oleic acid, stearic acid or arachidic acid. Alternatively, the shell may also be composed of or comprise fluorinated analogues of the above-mentioned lipids. In another preferred embodiment, the shell is composed of or comprises the above-mentioned lipids which are covalently linked to hydrophilic polymers such as polyethylene glycol (PEG), preferably PEG 2000-8000, e.g. dipalmitoyl or distearoyl phosphatidylethanolamine-polyethyleneglycol 5000. In a particularly preferred embodiment, the shell is composed of or comprises—preferably in an amount of from 50 to 100%, more preferably in an amount of 70 to 90%—negatively charged phospholipids, more preferably negatively charged phospholipids based on fatty acids having at least 14 carbon atoms, e.g. myristic acid, palmitic acid, stearic acid oleic acid or arachidic acid, e.g. dipalmitoyl phosphatidylglycerol or dipalmitoyl phosphatidylethanolamine-PEG. In another preferred embodiment, the shell comprises—preferably in an amount of from 1 to 20%—positively charged synthetic lipids, e.g. cationic lipids normally used in nucleic acid delivery such as DOTAP (N-1(-(2,3-dioleoyloxy)propyl)-N,N,N-trimethylammoniumethyl sulphate), DOTMA (N-(1-(2,3-dioleoyloxy)-propyl)-N,N,N-trimethylammonium chloride), DOGS (dioctadecylamidoglycyl spermine) and the like. Alternatively, the shell is composed of or comprises lipopeptides, for examples lipopeptides as described in WO-A-99/55383, the content of which is incorporated herein by reference.

The term "gas precursor" in the context of the present invention denotes a material which is a liquid or a solid at ambient temperature and pressure and changes phase from liquid to gas at the relevant temperature, e.g. the body temperature of the subject. When referring to "gas" and "gas precursor", it will be understood that mixtures of gases and gas precursors fall within the definition.

Suitably, microbubbles according to the invention comprise air, nitrogen and fluorinated compounds, either partially fluorinated or fully fluorinated (perfluorinated compounds), as pure compounds or mixtures thereof. In a preferred embodiment, the microbubbles comprise perfluorinated compounds, e.g. perfluoropropane, perfluorobutane, perfluoropentane, perfluorohexane, sulfur hexafluoride and the like, optionally in admixture with nitrogen.

The microbubbles according to the invention have a mean particle size of 0.25-15 μm in diameter, preferably 0.5-7 μm, particularly preferably 1-5 μm.

The microbubbles according to the invention have a pressure stability of at least 50% at a pressure of 120 mm Hg. In the context of the invention, the term "pressure stability of at least 50%" means that the acoustic attenuation efficacy of the microbubbles after being exposed to a pressure of 120 mm Hg is at least 50% of the acoustic attenuation efficacy of said microbubbles before being exposed to said pressure. Hence, by comparing the acoustic attenuation efficacy of the microbubbles before and after exposure to pressure, a measure of the microbubble's ultrasound imaging efficacy can be obtained. The acoustic attenuation efficacy can be determined by measuring the dampening (dB/cm) of a sound beam going through a diluted suspension of the microbubble sample using one or two broad band transducers with centre frequencies 3.5 and/or 5.0 MHz. Transmission is measured by pulse-echo technique; short pulses of sound are emitted from the transducer and traversed through a measuring cell compartment before being reflected from the back wall of the compartment and received again by the emitting transducer. The pulses are digitised by an oscilloscope and frequency spectra are calculated by Fourier transformation. To compensate for transmission path and transducer characteristics, the spectra are normalised to spectra of the pure diluent. A detailed description of the measurement of attenuation spectra and a suitable system setup for is described in L. Hoff, Acoustic Characterization of Contrast Agents for Medical Ultrasound Imaging, Kluwer Academic Publishers, 2001, chapter 4, page 99-109, the disclosure of which is incorporated herein by reference. The analysis is normally conducted in the range of 0° C. to 50° C., preferably at ambient room temperature. In a first step of the analysis, a reference spectrum is taken from the diluent. Suitable diluents are free of air bubbles and any liquids in which the microbubbles are stable could be used, preferable diluents are isotonic saline solution like Isoton II (Coulter Electronics Ltd. Luton, UK), a 0.9% saline solution comprising a phosphate buffer and a detergent to reduce surface tension. In a next step, the microbubble sample is mixed with the diluent and one or more attenuation spectra are measured at ambient pressure. The concentration of the microbubble sample is adapted to the size of the microbubbles. Preferably, the dilution factor is such that the attenuation from the microbubble sample is between 15 and 20 dB, i.e. about 3 dB/cm. This typically means that the microbubbles are diluted by a factor $10^3$ to $10^4$. In a next step, the pressure is raised to 120 mm Hg and one or more attenuation spectra are measured. In order to determine the pressure stability according to the invention, the acoustic attenuation efficacy of the microbubble sample before pressure is set to 100% thus allowing the calculation of the relative acoustic attenuation efficacy of the microbubble sample after pressure.

In a preferred embodiment, the microbubbles according to the invention have a pressure stability of at least 70%, more preferred of at least 85%, most preferred of at least 95%.

In a preferred embodiment, the microbubbles according to the invention are stable for pressure variations associated with ultrasound imaging of a mechanical index of at least 0.2. A method to determine the microbubble stability associated with ultrasound imaging pressures is described in W. T. Shi et al., Ultrasound in Med. & Biol., Vol. 26, 2000, 1-11.

Suitably, the microbubbles according to the invention are echogenic, i.e. they are capable of scattering or reflecting ultrasound waves. Preferably, the microbubbles are adapted to return a signal at a frequency different from the transmit frequency of the ultrasound pulse. That is, the microbubbles are adapted for harmonic ultrasound imaging as described in U.S. Pat. No. 5,540,909.

The microbubbles according to the invention can be prepared in a variety of ways which are readily apparent to those skilled in the art, including, e.g. shaking, vortexing, sonication, extrusion, repeated freezing and thawing cycles, extrusion under pressure through pores of defined size and spray drying. For example for lipid comprising microbubbles, the lipid-containing medium may be subjected to any appropriate emulsion generating technique, e.g. sonication, high pressure homogenisation, high shear mixing, in the presence of the selected gas or gas precursor. The gas employed in the emulsification step need not to be the same as in the final microbubble. Thus, most of this gas may be removed during a subsequent lyophilisation step and residual gas may be removed by evacuation of the dried product, to which an atmosphere or overpressure of the desired end product gas may then be applied (see for example WO-A-97/29783, the content of which is incorporated herein by reference).

Other methods of forming the microbubbles according to the invention includes the formation of protein comprising microbubbles (EP-A-359 246 and U.S. Pat. No. 4,718,433), the formation of lipid containing microbubbles (U.S. Pat. No. 4,684,479) and the formation of liposomal microbubbles (U.S. Pat. No. 5,088,499; U.S. Pat. No. 5,123,414 and WO-A-94/28874), the content of which is incorporated herein by reference.

According to the method of the invention, the microbubbles are administered in form of a preparation, preferably in form of a liquid preparation. In the following, the term "preparation" is used interchangeably with the term "microbubble preparation".

Preparations according to the invention comprise the above-described microbubbles and one or more components selected form the group consisting of osmotic agents, stabilisers, surfactants, buffers, viscosity modulators, emulsifiers, solubilising agents, suspending agents, wetting agents, antioxidants, viscosity increasing agents, tonicity raising agents, salts, sugars and the like. Such components are added to ensure maximum life and effectiveness of the microbubbles. Additionally, considerations as sterility, isotonicity and biocompatibility may govern the use of such components.

Suitable viscosity modulators include, for example, carbohydrates and their phosphorylated and sulfonated derivatives; polyethers, preferably with molecular weight ranges between 400 and 100.000 and di- and trihydroxy alkanes and their polymers, preferably with molecular weight ranges between 200 and 50.000.

Suitable emulsifying and/or solubilizing agents include, for example, acacia, cholesterol, glyceryl monostearate, lanolin alcohols, lecithin, mono- and diglycerides, ethanolamine, diethanolamine oleic acid, oleyl alcohol, poloxamer, for example, poloxamer 188, poloxamer 184, and poloxamer 181, polyoxyethylene 50 stearate, polyoxyl 35 castor oil, polyoxyl 10 oleyl ether, polyoxyl 20 cetostearyl ether, polyoxyl 40 stearate, polysorbate 20. polysorbate 40. polysorbate 60. polysorbate 80. propylene glycol diacetate, propylene glycol mono stearate, sodium lauryl sulfate, sodium stearate, sorbitan mono-laurate, sorbitan mono-oleate, sorbitan mono-palmitate, sorbitan monostearate, stearic acid, trolamine, emulsifying wax, and the like.

Suitable suspending and/or viscosity-increasing agents include, for example, acacia, agar, alginic acid, aluminum mono-stearate, bentonite, magma, carbomer 934 P, cellulose, methylcellulose, carboxymethylcellulose, hydroxyethyl cellulose, hydroxypropyl methylcellulose, carrageenan, dextran, gelatin, guar gum, locust bean gum, veegum, magnesium-aluminum-silicate, silicon dioxide, zeolites, pectin, polyethylene oxide, povidone, propylene glycol alginate, sodium alginate, tragacanth, xanthan gum, alpha-d-gluconolactone, glycerol and mannitol.

Suitable suspending agents are for example polyethylene glycol (PEG), polyvinylpyrrolidone (PVP), polyvinyl alcohol (PVA), polypropylene glycol (PPG), polysorbate and the like.

Suitable tonicity raising agents which stabilise and add tonicity are, for example, sorbitol, mannitol, trehalose, sucrose, propylene glycol and glycerol.

The preparations according to the invention may further comprise dyes or biologically active agents, preferably selected from the group consisting of analgesics, antibiotics, leukotriene inhibitors or antagonists, antihistamines, antiinflammatories, antineoplastics, anticholinergics, anesthetics, enzymes, steroids, genetic material, viral vectors, antisense agents, proteins and peptides.

In a preferred embodiment, the preparations further comprise compounds which promote macrophage uptake, e.g. mannans, for example zymosan, mannose-containing oligo- and polysaccharides, Fc (fragment crystallizable) portions of immunoglobulin molecules, complement components, for example C3b or C3bi, ligands for scavenger receptors, ligands for toll-like receptors, ligands for LRPs (LDL-receptor-like proteins), bacterial glycopeptides or lipopolysaccharides for example bleomycin or endotoxin.

The preparations are preferably sterile injectable formulations like suspensions or emulsions comprising suitable carriers including non-toxic parenterally-acceptable aqueous or non aqueous solutions and the components and/or compounds described above. Preferred carriers are water or saline.

The preparations may be formulated according to known methods. In a preferred embodiment, the preparations are manufactured immediately before use. Thus, a dry microbubble product may be mixed with a suitable carrier and one or more of the above mentioned compounds and components. In another preferred embodiment, preparations are manufactured immediately before use and microbubbles are generated in situ during the manufacture of the preparation, e.g. by adding a suitable carrier to a vial containing the desired gas and the components comprising the shell of the microbubbles and agitating this mixture. The preparations according to the invention are preferably sterilised before administration and/or are manufactured from sterile starting materials. Sterilisation of the preparations may be achieved by filtration through a bacteria-retaining filter, by incorporating sterilising agents, by irridation and the like.

Administration according to step a) of the method of the invention can be carried out in various fashions which are not intravascular. Methods of parenteral administration are preferred and include but are not limited to the following routes: intramuscular, percutaneous, directly in a lymphatic vessel, interstitially, intraperitoneal, intrathecal, subcutaneous, intrasynovial, transepithelial (including transdermal) dermal, intradermal, subdermal, in a tumour or pathologic process itself, and the like. Preferably, the preparation is interstitially administered, preferably by interstitial injection including subcutaneous and intradermal injection. In the case of cancer patients, the preparation is preferably injected in proximity to the cancer (peritumoural). The preparation can also be injected by a combination of two or more parenteral modes, for example intramuscular, subcutaneous, and in the pathologic process, ensuring its accretion in the sentinel lymph node.

The preparation will normally be administered at a site and by means that ensure that it is mobilised and taken up into the lymphatic circulation. This will vary with the system to be imaged. Multiple injection sites may be preferable in order to permit proper drainage to the regional lymph nodes under investigation. In some cases, injections around the circumference of a tumour or biopsy site is desired. In other cases, injection into a particular sheath or fossa is preferred. Injection into the webs of the fingers or toes is a common mode used to study peripheral lymphatics. The preparation can be administered to the subject either pre-operatively and/or intra-operatively to localise the sentinel lymph node. The method according to the invention allows immediate and real-time identification of the sentinel lymph node following administration of the preparation in a region of interest as administration does not require significant lead time to reach the sentinel lymph node. Moreover, additional methodology can be employed to modify or alter the transport of the preparation to the sentinel lymph node, including massaging the injection site or stimulating flow. Preferably, the site of injection of the preparation will be massaged.

The method of the invention has applicability in locating the sentinel node associated with breast tumour. Images of axillary, subclavian and supraclavicular nodes may be obtained by injecting the preparation into and around the tumour and below the skin adjacent to the tumour. A unilateral injection can be made in the subcostal site ipsilateral to the tumour, followed by bilateral lymph node imaging. By injecting the preparation in the vicinity of the tumour, the practitioner will know that the lymph duct involved and leading to the sentinel node will be directed toward the axillary, internal mammary, or supraclavicular chain wherein ultrasound detection is effected at appropriate times after each injection.

Another approach is to inject the preparation around the areola tissue of the breasts bilaterally, and then detecting the axillary, internal mammary, or supraclavicular chains. In addition to periareolar injection, interdigital administration of the preparation may be used for visualization of axillary lymphatics (see, DeLand et al., (1980), Cancer Res. 40:2997-3001). Combined interdigital and periareolar administration of the preparation can provide increased accuracy to demonstrate increased uptake in affected axillary nodes. Intratumoural injection of the contrast agent can also be performed in patients with breast cancer or melanoma.

The preparations will be administered in an effective amount, i.e. in an amount which allows sufficient detection. It is anticipated that between 0.1 to 30 ml of the preparations are administered in liquid form, preferably 0.1 to 3 ml, particularly preferably 0.5 to 1.5 ml. The particularly preferred volume for administration corresponds to an administered microbubble gas volume of about from 5 to 15 µl. In a preferred embodiment, multiple injections are performed (typically 4), each with a small quantity of the preparation, e.g. 0.1 to 3 ml are administered to a subject per injection site. Variations can be due to the number of injections and the injection site. Other amounts of the preparations, such as from about 0.005 ml/kg to about 1.0 ml/kg, are also contemplated according to the method of the invention. Volumes of the preparations in liquid form will normally vary being dependent upon, e.g., the site of administration, the concentration of the preparation, the number of injections, the composition of the preparation and/or the type of microbubbles present therein and the properties peculiar to each individual subject.

In step b) according to the method of the invention, the microbubbles are allowed to accumulate in the sentinel lymph node.

After administration, the microbubbles do not require significant lead time to reach the sentinel lymph node and accumulate therein. Thus, immediate and real-time identification of the sentinel lymph node following administration of the preparation according to the invention is possible. Generally, the microbubbles according to the invention are capable of accumulating in the sentinel lymph node in less than 60 minutes. In a preferred embodiment, the microbubbles according to the invention accumulate in the sentinel lymph node in less than 15 minutes and particularly preferably in less than 5 minutes.

After administration, the microbubbles according to the invention have a half life of at least 5 minutes, preferably of at least 15 minutes and particularly preferably of at least 60 minutes.

As the accumulation time of the microbubbles in the sentinel lymph nodes is relatively short, the microbubbles according to invention allow imaging shortly after administration, improving logistics and prolonging the detection time.

In step c) according to the method of the invention, the microbubbles are detected in the sentinel lymph node using ultrasound imaging and thereby identifying the sentinel lymph node.

With respect to ultrasound, ultrasound imaging techniques contemplated for use in the present invention are well known in the art, and are described, for example, in McGahan and Goldberg, Diagnostic Ultrasound: A Logical Approach (Lippincott-Raven Publishers 1998), and in Frederick and Kremkau, Diagnostic Ultrasound: Principles and Instruments, (W B Saunders Co. 1998). Specific ultrasound imaging modes useful with the disclosed invention include harmonic or non-linear imaging, grey scale (B-mode), Doppler (including pulsed wave, power, flow, colour, amplitude, spectral and harmonic), 3-D imaging, gated imaging, and the like. With respect to non-linear imaging, it will be appreciated that the present invention is compatible with wideband harmonic imaging and pulse inversion harmonic imaging.

If one desires to use harmonic imaging and the ultrasound imaging machine is set to image at a particular frequency, the outgoing waveform supplied to the sonic transducer can be a numerical fraction of the imaging frequency (e.g., ½, ⅔, ⅓, and the like) or a whole number or fractional multiple of the imaging frequency (e.g., 2, {fraction (3/2)}, 3, 4, and the like). With any particular combination of microbubble preparation and excitation frequency, certain harmonics will be dominant. The second harmonic is a common example. Those strongest harmonics are preferred for obvious reasons, although other harmonics or frequencies may be selected for reasons such as preparation of multiple images or elimination of background. Moreover several frequencies, including harmonic and non-harmonic frequencies or some combination thereof, may be simultaneously detected to provide the desired image. That is, in preferred embodiments any frequency other than the interrogation frequency may be used to provide the desired data. Of course, those skilled in the art will appreciate that dominant harmonics can be determined by simple empirical testing of the contrast agent preparation.

To detect the re-radiated ultrasound energy generated by the microbubble preparations, a modified conventional ultrasound scanner system or commercially available non-linear imaging systems can be used. These systems are able to detect or select one or more or all of the new frequencies, or harmonics, radiated by the microbubble preparation for production of the ultrasound image. In other words, it detects a frequency different from the emitted frequency. Equipment suitable for harmonic ultrasound imaging is disclosed in WO-A-91/15999. Many conventional ultrasound imaging devices, however, utilise transducers capable of broad bandwidth operation, and the outgoing waveform sent to the transducer is software controlled. For this reason, reprogramming to emit a waveform different from the one detected is well within the level of skill in the art.

Although non-linear ultrasound imaging such as harmonic ultrasound imaging, second harmonic ultrasound imaging or preferably pulse inversion is particularly preferred for use in the disclosed methods, other types of ultrasound conventional imaging such as B-mode (gray scale imaging), F-mode (colour flow or Doppler imaging) and D-mode (spectral Doppler) are also compatible and within the purview of the present invention.

In B-mode imaging, the ultrasound system typically transmits a series of beams, along scan lines, steered to scan a desired field of view. The ultrasound system typically steers "receive beams" in a manner that corresponds to the transmit beams. Data returned from each receive beam is communicated to an image display subsystem which reconstructs a two-dimensional gray scale image from the B-mode data and displays it on a console. Such series of pulses down a single line may be identical or may be of equal or unequal frequency or have a near 180 degree phase shift (inverted pulse) to promote the distinction of the contrast agent from the surrounding tissues.

F-mode imaging is accomplished in a manner similar to B-mode imaging, in that the ultrasound system fires and receives a series of beams to scan a field of view. However, since F-mode imaging requires calculation of the velocity of targets, each line is fired and received several times. As with B-mode imaging, the data returned from each firing of each line is used to reconstruct an image on a console.

F-mode imaging is often used concurrently with B-mode imaging. For example, the gray scale image reconstructed from a B-mode scan can be superimposed with an F-mode image reconstructed from an F-mode scan of the same field of view or of a lesser included field of view. The F-mode information can be displayed using colours, with different colours indicating different positive or negative flow velocities or turbulence at the part of the B-mode image on which the pixel is superimposed. Because F-mode imaging is intended to provide only qualitative insight into target motion in the patient's body, the ultrasound system's processing of F-mode signals need not have high spatial or velocity resolution either in amplitude or in pixel resolution. However, since an important value of F-mode imaging is to detect flows relative to anatomical structures in the body, it is usually important that the F-mode image be properly registered with the B-mode image on-screen. Since this technique relies on the correlation of signal obtained from one pulse versus the subsequent pulse, and since microbubbles can be destroyed by the first pulse, an F-signal is generated that is not related to motion. This loss of correlation can be shown in a variety of display formats but is typically displayed in colour.

In D-mode (spectral Doppler) acquisition, the ultrasound system fires a beam and processes the return signal for a single target. Spectral Doppler information can be obtained by transmitting and receiving either continuous wave (CW)

or pulsed wave (PW) ultrasonic energy. In CW Doppler acquisition, for example, Power Doppler (Doppler angiography), the ultrasound receiver continuously receives echoes from all objects within the receiver's area of sensitivity in the body, and cannot isolate information received from any specific range interval. CW Doppler is most useful where the instrument's area of sensitivity can be adjusted, either by physical placement of the probe or by beamforming, or both, to include only the desired target. In PW Doppler acquisition, the ultrasound instrument receives echoes from individual pulses, the timing of which implies a range interval within the body of the object which produced the echo. A clinician typically selects a range interval within which the target is expected to be located.

In D-mode acquisition, it is desirable to be able to produce detailed quantitative measurements over a very large range of signal levels (dynamic range). D-mode information is processed by the ultrasound system to display either the velocity spectrum of the target, plotted against time, or to provide an audio output carrying similar information. Spectral Doppler acquisition is described in L. Hatle, and B. Angelsen, "Doppler Ultrasound in Cardiology" (1st ed. 1982) and (2d ed. 1984).

In addition to B-, F- and D-mode acquisition, a fourth mode also exists, known as M-mode, but this is merely a different display modality for data acquired in a manner similar to B- or F-mode acquisition. The requirements for M-mode acquisition are not significantly different from those for B- or F-mode acquisition. Alternatively, or in addition, 3-dimensional ultrasound is also contemplated, wherein 3-D scans require special probes and software to accumulate and render the images. It will be appreciated that the emitted ultrasound energy—if sufficiently high—may disrupt the microbubbles present in the lymphatics. Doppler based imaging methods as described above may detect this as a "pseudo Doppler" signal allowing sensitive and specific detection of the microbubbles that are immobilised or moving very slowly (see for example U.S. Pat. No. 5,425,366).

Additional techniques contemplated for use in the present invention are well known in the art, and are described, for example, in Gamsu et al., Diagnostic Imaging Review (W. B. Saunders Co 1998).

Ultrasonic energy may be applied to at least a portion of the subject to image the target tissue. A visible image of an internal region of the subject may then be obtained, such that the identification of the sentinel lymph node can be ascertained.

Another aspect of the invention is a method for the identification of a sentinel lymph node in a subject preadministered with microbubbles comprising a shell and a gas or gas precursor, said microbubbles having a mean particle size of about 0.25-15 µm in diameter and a pressure stability of at least 50% at a pressure of 120 mm comprising detecting said microbubbles accumulated in said sentinel lymph node of said subject using ultrasound.

The method according to the invention it is not only useful to identify the sentinel lymph node, but also to determine whether said sentinel lymph node shows defects or irregularities in the lymphatic structure. Thus, the present invention also provides a method for the discrimination between benign and malignant sentinel lymph nodes in a subject comprising a) administering to said subject a preparation comprising microbubbles comprising a shell and a gas or gas precursor, said microbubbles having a mean particle size of about 0.25-15 µm in diameter and a pressure stability of at least 50% at a pressure of 120 mm Hg, b) allowing said microbubbles to accumulate in said sentinel lymph node, c) detecting said microbubbles in said sentinel lymph node using ultrasound and d) characterising said sentinel lymph node as being benign or malignant according to the pattern of contrast enhancement within the lymph node.

Mattrey et al. noticed during sentinel lymph node ultrasound imaging that cancer within the node did not fill with contrast agent material, thus leaving a filling defect. However, it was stated that further work is required for confirmation. (R. Mattrey et al., Academic Radiology 9, 2002, S231-S235). It was now found that it is possible to classify the sentinel lymph nodes after having identified them according to the method of the invention because of their different patterns of contrast enhancement: benign sentinel lymph nodes appear uniformly echogenic while malignant sentinel lymph nodes demonstrate a heterogenic enhancement pattern with both, areas of increased echogenity and areas that do not enhance. This finding represents a major clinical advance as the method according to the invention not only allows for noninvasive and safe detection of sentinel lymph nodes, but also of their metastatic infiltration.

The above-mentioned method provides good results just by visual assessment of acquired ultrasound images. Discrimination between benign and malignant lymph nodes may be further improved by application of image processing methods to enhance the difference in pattern of contrast enhancement between normal and infiltrated nodes.

The invention will now be described in greater detail by reference to the following non-limiting examples.

EXAMPLES

Example 1

Pressure Stability Measurements

Various ultrasound contrast agents containing microbubbles were tested for pressure stability:

Albunex™, microbubbles containing air in a shell of denatured human serum albumine, which can be prepared as disclosed in EP-A-359 246.

Sonovue™, microbubbles containing $SF_6$ encapsulated in a phospholipid membrane Sonazoid™, microbubbles containing perfluorobutan encapsulated in a surfactant membrane a) Size Distribution and Volume Concentration Determination The microbubble concentration and size distribution of all samples were determined by Coulter counting with a Coulter Multisizer Mark II (Coulter Electronics Ltd., Luton, England) fitted with a 50 µm aperture with a nominal measuring range of 1 to 30 µm. Analysis was performed with 64 logarithmically spaced size channels. A 20 µl sample was diluted in 200 ml Isoton II (Coulter Electronics) at ambient room temperature and stirred for 4 minutes before analysis. As analytic response, the microbubble volume concentration as a percentage of suspension volume and the volume median diameter of the microbubbles were used.

| | microbubble volume concentration as a percentage of suspension volume [%] | volume median diameter of the microbubbles [µm] |
| --- | --- | --- |
| Albunex™ | 0.7 | 10 |
| Sonovue™ | 0.6 | 7 |
| Sonazoid™ | 1.0 | 3 | b) Acoustic Attenuation Measurements

The acoustic attenuation spectrum of all samples was measured as described by L. Hoff, Acoustic Characterization of Contrast Agents for Medical Ultrasound Imaging, Kluwer Academic Publishers, 2001, chapter 4. The acoustic attenuation of a sound beam going through a diluted suspension of the samples was measured using a broadband transducer with a centre frequency of 3.5 MHz. A suitable sample volume was homogeneously dispersed in 55 ml Isoton II at ambient room temperature before analysis. Transmission was measured by a pulsed-echo technique; short pulses of sound were emitted from the transducer and traversed the measuring cell compartment before being reflected from the back wall of the compartment and received again by the emitting transducer. The pulses were digitised by an oscilloscope and frequency spectra were calculated by Fourier transformation. To compensate for transmission path and transducer characteristics, the spectra were normalised to the spectra of pure Isoton II. Results were normalised to a 1:1000 dilution. The acoustic attenuation [dB/cm] at atmospheric pressure was measured at 3.5 MHz and the obtained measurement reading was set to 100% acoustic attenuation efficacy. After application of a pressure of 120 mm Hg for 30 seconds, the attenuation was measured again and the acoustic attenuation efficacy after pressure was calculated. Pressure stability was reported as attenuation efficacy after pressure in percent of attenuation efficacy before pressure.

|  | Pressure stability at 120 mm Hg [%] |
| --- | --- |
| Albunex ™ | 0 |
| Sonovue ™ | 79 ± 2 |
| Sonazoid ™ | 98 ± 1 |

Example 2

In Vivo Sentinel Lymph Node Detection and Characterization

Anaesthetised Sinclair pigs with melanoma tumours were used to investigate sentinel lymph node detection and characterisation using Sonazoid™.
a) In Vivo Sentinel Lymph Node Detection 1 ml Sonazoid™ was administered intradermally around the primary tumour. After 5 minutes of gentle massage of the injection site, ultrasound scanning was performed with a Siemens Elegera scanner. The sentinel lymph node showed strong contrast enhancement on pulse inversion gray scale imaging and was further evaluated with high power colour flow imaging which gave a mosaic enhancement pattern characteristic of microbubble rupture. The identification of the sentinel node was further aided by contrast enhancement of the lymph canal from the injection site to the sentinel node. The location of the lymph node was marked on the skin. The location of the sentinel node was confirmed with peritumoural injections of radiocolloid tracer and blue dye in accordance with current clinical practice. The contrast enhancement of the sentinel lymph node was present for up to 3 hours.

The method described in example 2a was applied in 6 melanoma Sinclair pigs. 17 primary tumours with 31 melanomas were assessed using ultrasound, lymphoscintegraphy and blue dye (the gold standard). The accuracy of correctly identifying the sentinel nodes was 90% for ultrasound and 81% for lymphocintegraphy.

b) In Vivo Sentinel Lymph Node Detection and Characterization 1 ml Sonazoid™ was administered intradermally around each primary tumour in a Sinclair pig with 3 melanoma tumours. After 5 minutes of gentle massage of the injection site, ultrasound scanning was performed with a Siemens Elegera scanner and the sentinel nodes identified as described in Example 2a. One of the lymph nodes showed a homogenous contrast enhancement pattern, while the other two showed a spotty, heterogeneous enhancement pattern. The first node was characterised as normal, while the two latter were characterised as malignant based on ultrasound imaging. Microscopic histological examination of the lymph nodes confirmed absence of tumour in the first node and the presence of tumour in the two latter nodes. The pathological evaluation produced a pseudocolor map of the pathology specimens that correlated well with the contrast enhancement patterns seen on ultrasound with contrast enhancement of normal lymphatic tissue and absence of enhancement in tumour tissue.

The method described in example 2b was applied in 6 melanoma Sinclair pigs. In total 31 lymph nodes were investigated. The accuracy of correctly detecting the presence or absence of metastatic melanoma tumours in the lymph nodes was 86%.

There were no statistically significant difference between contrast enhanced ultrasound and pathology.

Example 3

Comparison of Albunex™ and Sonazoid™

1 ml Albunex™ as described in Example 1 was injected interdigitially in the hind limb of an anesthesised dog. The injection site was gently massaged for 5 minutes. The draining lymph node (Inn popliteus) was imaged with an ATL HDI 5000 Scanner equipped with a L12-5 transducer operating in pulse inversion mode. No contrast enhancement was seen at imaging 5 and 15 minutes post injection, respectively.

20 minutes after the Albunex™ injection, 1 ml Sonazoid™ as described in Example 1 was injected interdigitially in the same hind limb following identical imaging procedures as described in Example 3a. A strong contrast enhancement was seen at imaging 5 minutes post injection and enhancement was maintained at imaging 15 minutes post injection. Peak contrast enhancement was more than 7 dB.

What is claimed is:
1. Method for the identification of a sentinel lymph node in a subject comprising
   a) administering to said subject a composition comprising microbubbles comprising a shell and a gas or gas precursor, said microbubbles having a mean particle size of about 0.25-15 μm in diameter and a pressure stability of at least 50% at a pressure of 120 mm Hg, and wherein the shell comprises negatively charged phospholipids in an amount of from 50-100%,
   b) allowing said microbubbles to accumulate in said sentinel lymph node,
   c) detecting said microbubbles in said sentinel lymph node using ultrasound, and
   d) characterizing said sentinel lymph node as being benign or malignant according to the pattern of contrast enhancement within the lymph node.
2. Method according to claim 1 wherein the composition is percutaneously administered.

3. Method according to claim 1, wherein the microbubbles are stable for pressure variations associated with ultrasound imaging of a mechanical index of at least 0.2.

4. Method according to claim 1, wherein the composition further comprises a macrophage stimulating compound.

5. Method according to claim 1, wherein the composition is interstitially administered.

6. Method according to claim 1, further comprising applying image processing methods to enhance the difference in pattern of contrast enhancement between benign and malignant lymph nodes.

7. Method according to claim 1, wherein the benign sentinel lymph nodes appear uniformly echogenic while malignant sentinel lymph nodes demonstrate a heterogenic enhancement pattern with both areas of increased echogenity and areas that do not enhance.

* * * * *